United States Patent [19]
Chien et al.

[11] Patent Number: 5,762,956
[45] Date of Patent: Jun. 9, 1998

[54] TRANSDERMAL CONTRACEPTIVE DELIVERY SYSTEM AND PROCESS

[75] Inventors: Yie W. Chien, North Brunswick; Te-Yen Chien, Branchburg; Sai-Jun Gong, Piscataway, all of N.J.

[73] Assignee: Rutgers, The State University of New Jersey, New Brunswick, N.J.

[21] Appl. No.: 638,009

[22] Filed: Apr. 24, 1996

[51] Int. Cl.⁶ .................................................. A61F 13/00
[52] U.S. Cl. ........................ 424/449; 424/448; 514/946; 514/947
[58] Field of Search .................... 424/448, 449; 514/946, 947

[56] References Cited

U.S. PATENT DOCUMENTS

| | | | |
|---|---|---|---|
| 4,818,540 | 4/1989 | Chien et al. | 414/449 |
| 4,906,169 | 3/1990 | Chien et al. | 424/448 |
| 4,906,475 | 3/1990 | Kim | 424/449 |
| 5,296,230 | 3/1994 | Chien et al. | 424/448 |
| 5,314,694 | 5/1994 | Gale | 424/448 |

*Primary Examiner*—D. Gabrielle Phelan
*Attorney, Agent, or Firm*—Schwegman, Lundberg, Woessner & Kluth, P.A.

[57] ABSTRACT

A transdermal contraceptive delivery system (TCDS) for fertility control in women is described comprising a backing layer, an adjoining layer of a solid absorption adhesive polymer matrix in which minimum effective daily doses of an estrogen and a progestin are dispersed and released for transdermal absorption. Presently preferred is use of the natural estrogen, 17-beta-estradiol, and the synthetic progestin, levonorgestrel. Along with these two steroidal contraceptive agents, a combination of several chemical skin permeation enhancing agents, blended at specific weight ratios, are homogeneously dispersed in the adhesive polymer matrix. The invention also provides a process of fertility control utilizing the transdermal contraceptive delivery system.

26 Claims, 7 Drawing Sheets

Physical Structure of Transdermal Contraceptive Delivery System

Physical Structure of Transdermal Contraceptive Delivery System

- Drug-impermeable backing laminate
- LNG and $E_2$ in polymer matrix
- Drug-impermeable release liner 17-ß Estradiol Levonorgestrel

TRANSDERMAL CONTRACEPTIVE DELIVERY SYSTEM AND PROCESS

BACKGROUND ART

Control of fertility continues to be an important issue throughout the world even though the population growth rate has shown a steady decline in many countries, partly owing to the extensive use of oral contraceptives. The efficacy of these contraceptives depends on the type and dose of hormonal ingredients. The first oral contraceptives to be marketed were progestin-estrogen combinations, and the majority of currently marketed products are of this type. The two substances are present in various ratios and act principally by inhibiting ovulation in normally cycling women. Estrogen is usually present in relatively high doses in these contraceptives, which are nearly 100% effective when taken correctly. However, there is a small probability of ovulation and hence, conception, if a single pill is missed, and thus any failures are generally attributable to the negligence of the user.

Since over 90% of the natural estrogen taken orally is destroyed in the digestive tract or in the liver, a large excess must be administered in order to provide an effective dosage orally. This overdosing results in uncertain effectiveness and the creation of a large quantity of undesirable metabolites. Therefore, a synthetic estrogen is ordinarily used as the estrogen component in combination contraceptive preparations. Similarly, in the case of orally administered progestin, a substantial amount of metabolic breakdown occurs causing undesired metabolic products. Therefore, orally administered contraceptive products necessarily contain either "overdoses" of natural estrogen and progestin or synthetic forms of these hormones to provide the desired fertility control.

Although the combination of a progestin and estrogen is very effective in suppressing ovulation, certain undesirable side effects became apparent on widespread usage of this type of oral contraceptive. The incidence of thromboembolic and related vascular disorders, including stroke and myocardial infarction, is higher in women using oral contraceptives; the relative risk may be eleven times greater in users as compared to a control population. Further, the risk increases sharply in women over 35 years of age. Contraceptive use has also been associated with increased evidence of benign liver tumors and an increased risk of gallbladder disease. Additionally, fetal abnormalities may result if the mother continues to take the pill after becoming pregnant. Finally, some possible, but unproven complications of contraceptive use include breast cancer, and cancer of the uterus, cervix and vagina.

An ideal and patient-acceptable fertility control system should provide the following advantages: minimized side effect, increased ease of administration, rapid termination of treatment, and improved patient compliance. In recent years, considerable attention has been directed to the development of implantable, intrauterine, intracervical or intravaginal fertility control delivery systems to provide a prolonged and controlled administration steroidal hormones to the body for achieving fertility control. However, none of the delivery systems developed so far can be considered ideal and side effect-free.

On the other hand, absorption of pharmaceuticals through the skin, i.e., transdermal drug delivery, provides avoidance of many undesirable side effects. Specifically, transdermal rate-controlled drug administration provides: (i) avoidance of the risk and inconvenience of intravenous therapy and of the variability in absorption and metabolism associated with oral therapy; (ii) continuity of drug administration, permitting the use of a pharmacologically-active agent with short biological half-life; (iii) efficacy can be achieved with lower total daily dosage of drug, since there is reduced degradation in the digestive system; (iv) less chance of over- or under-dosing; (v) provision of a simplified medication regimen; and (vi) ability to rapidly terminate the drug infusion, if needed, by removal of the drug delivery system from the skin surface.

It is, therefore, highly desired that transdermal systems be provided which permit 1) use of the natural estrogen, 17-beta-estradiol, 2) use of a minimum number of dosage units for each menstrual cycle, and 3) that provide sufficiently high levels of estrogen and progestin hormones to provide high assurance of fertility control without a high amount of undesired metabolic or chemical degradative products.

SUMMARY OF THE INVENTION

The present invention is directed to a transdermal contraceptive delivery system (TCDS) and a method of fertility control utilizing the TCDS of the present invention. The system comprises a backing layer, and an adhesive polymer matrix which has dispersed therein hormones effective for controlling fertility, as well as a combination of skin permeation enhancers. As well as providing the matrix within which the hormones and skin permeations are dispersed, the adhesive polymer matrix also serves to adhere the delivery system in intimate contact with the skin of the subject being treated to permit the hormones to be absorbed transdermally.

Preferably, the materials used for the backing layer are laminates of such polymer films with a metal foil such as aluminum foil. It is further preferred that the backing layer will be a thickness of from about 10 to about 200 microns. Preferably, the thickness will be from about 20 to about 150 microns, and more preferably, will be from about 30 to about 100 microns.

It is preferred that the adhesive polymer matrix be fabricated from biologically acceptable adhesive polymers, such as polyacrylic adhesive polymers, silicone adhesive polymers or polyisobutylene adhesive polymers. Preferably, the adhesive polymer layer is fabricated from a polyacrylate adhesive. More preferably, the polyacrylate adhesive will be of the general formula:

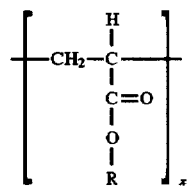

wherein x represents the number of repeating units sufficient to provide the desired properties in the polymer, and R is H or a lower ($C_1$–$C_{10}$) alkyl groups chosen from the group consisting of ethyl, butyl, and ethylhexyl. Most preferably, the adhesive polymer matrix of the present invention comprises a polyacrylate adhesive copolymer wherein R is a 2-ethylhexyl group and the comonomer is vinyl acetate (about 3–60% w/w). The adhesive polymer matrix is solid and dimensionally stable, but is preferably thin, e.g. from about 10 to about 200 microns, preferably from about 20 to about 180 microns and most preferably from about 30 to about 150 microns in thickness.

It is preferred that the hormones utilized in the system of the present invention comprise an estrogen chosen from the group consisting of 17-beta-estradiol, ethynyl estradiol and biocompatible derivatives thereof, and a progestin. Most preferably the progestin is levonorgestrel or biocompatible derivatives thereof.

The adhesive polymer matrix of the present invention further comprises a moisture-regulating humectant/plasticizer dispersed therein. Preferably, the humectant/plasticizer will be a polyol. Most preferably the polyol will be polyethylene glycol, such as a liquid polyethylene glycol, with a molecular weight of about 200 to about 450. The inclusion of polyethylene glycol serves to control the rigidity of the polymer matrix, as well as acting as a moisture regulating humectant. Incorporation of a humectant in the adhesive polymer matrix allows the TCDS to absorb moisture on the surface of skin, which in turn helps to reduce skin irritation and to prevent the TCDS from falling off during long term (such as 7 days) use of the TCDS. The amount of humectant/plasticizer to be utilized will preferably be from about 0 to about 25%. More preferably, the amount of humectant/plasticizer utilized will be less than 5%, e.g., about 0.25–2.5% of the total adhesive polymer matrix.

The skin permeation enhancers utilized in the present invention consist of a combination of dimethyl sulfoxide (DMSO), a fatty alcohol ester of lactic acid and lower ($C_1$–$C_4$) alkyl ester of lactic acid. Preferably, the enhancer is a mixture of DMSO with lauryl lactate (available as Ceraphil 31 from Van Dyk Chem. Co., Belleville, N.J.) and ethyl lactate. Applicants have made the surprising discovery that the unique combination of skin permeation enhancers utilized in the present invention, when homogeneously dispersed in the adhesive polymer matrix at a particular ratio (preferably, 2.5–5:1:1, respectively), acts to solubilize the dispersed estrogen and progestin, thus greatly enhancing the skin permeation of the steroid hormones contained in the TCDS. Applicants have also discovered that the preferred skin permeation enhancer combination also enhances the tackiness and adhesion of the TCDS. The skin permeation mixture will be present in the adhesive polymer matrix in an effective amount of up to about 30–60% w/w of the total matrix, i.e., at about 35–55% w/w of the matrix.

Optionally, an additional adhesive layer can be formed using the same or a different adhesive polymer which is also biocompatible and placed in intimate contact with the surface of the hormone-containing adhesive polymer layer. This adhesive layer can contain one or more effective transdermal absorption enhancing agents or be free of these agents.

The adhesive polymer layers can be formed by any acceptable method available to the art, such as spraying, solvent casting or laminating. The concentration of the skin permeation enhancers can be reduced in the portion of the adhesive polymer layer, as may be necessary if less than desired adhesion is realized, by applying the surface portion of the adhesive layer separately wherein the adhesive composition has a lower concentration of skin permeation enhancers.

The invention further provides a method of controlling fertility by applying a series of the transdermal contraceptive delivery systems to the skin of a subject to be treated, whereby said hormones contained therein are transdermally administered in an amount effective to prevent pregnancy.

DETAILED DESCRIPTION OF THE INVENTION

Figure 1:
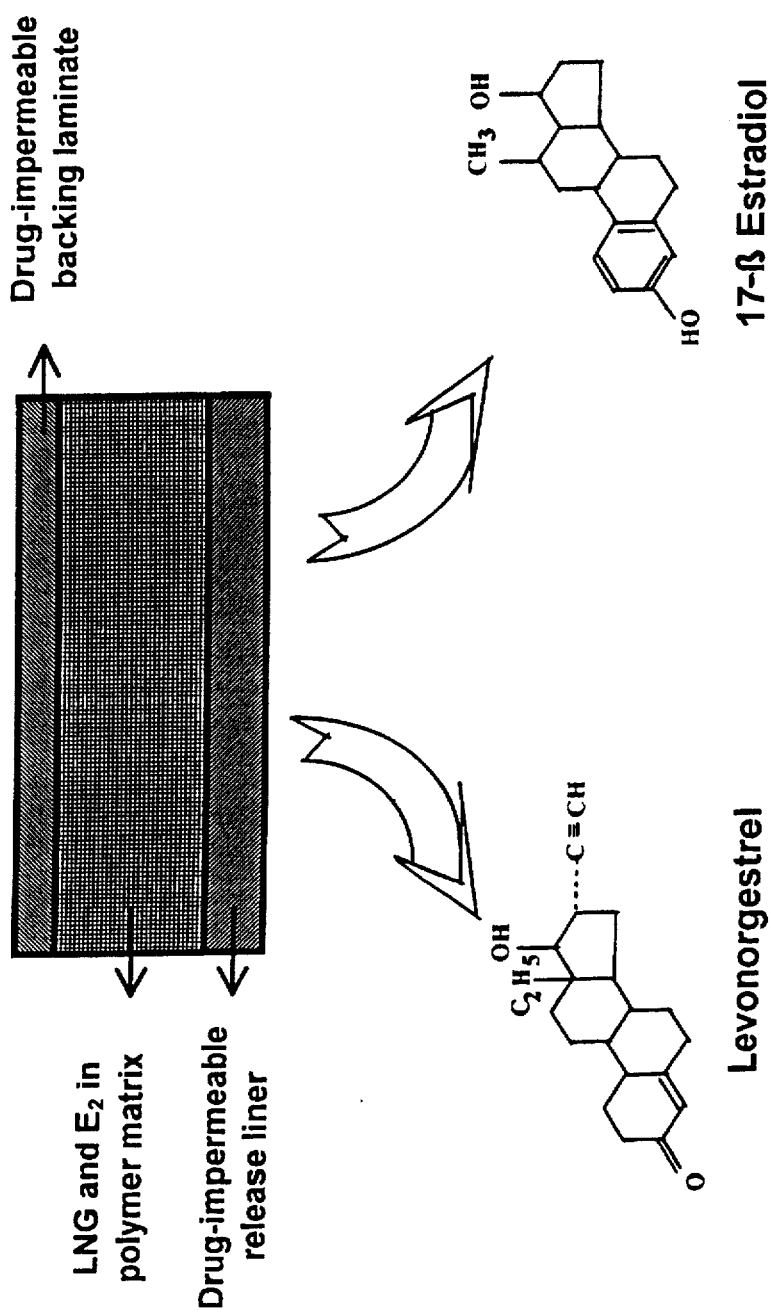
FIG. 1 is an illustration of the physical structure (side view) of the TCDS patch formulated and fabricated in Example 1.

The present invention is directed to a transdermal contraceptive delivery system (TCDS) comprising a backing layer and an adhesive polymer matrix which has dispersed therein hormones effective for controlling fertility as well as a combination of skin permeation enhancers.

The Backing Layer

The backing layer can be made of any suitable material which is impermeable to the hormones of the adhesive polymer matrix. The backing layer serves as a protective cover for the matrix layer and provides also a support function. The backing can be formed so that it is essentially the same size layer as the hormone-containing adhesive polymer matrix or it can be of larger dimension so that it can extend beyond the side of the adhesive polymer matrix or overlay the side or sides of the hormone-containing adhesive polymer matrix and then can extend outwardly in a manner that the surface of the extension of the backing layer can be the base for an adhesive means. For long-term applications, e.g., for seven days, it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns. Preferably, the thickness will be from about 20 to about 150 microns, and more preferably, will be from about 30 to about 100 microns.

Adhesive Polymer Layer

Generally, those polymers used to form the biologically acceptable adhesive polymer layer are those capable of forming thin walls or coatings through which hormones can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix would affect the release rate of the hormones as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like.

Preferably, the biologically acceptable adhesive polymer matrix should be selected from polymers with glass transition temperatures below room temperature. The polymer may, but need not necessarily, have a degree of crystal-linity at room temperature. Cross-linking monomeric units or sites can be incorporated into such polymers. For example, cross-linking monomers can be incorporated into polyacrylate polymers, which provide sites for cross-linking the matrix after dispersing the hormones into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, the adhesive polymer matrix comprises a polyacrylate adhesive polymer of the general formula (I):

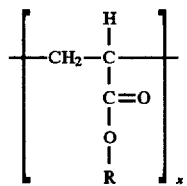

wherein x represents the number of repeating units sufficient to provide the desired properties in the adhesive polymer and R is H or a lower ($C_1$–$C_{10}$) alkyl, such as ethyl, butyl, 2-ethylhexyl, octyl, decyl and the like. More preferably, the adhesive polymer matrix comprises a polyacrylate adhesive copolymer which comprises a 2-ethylhexyl acrylate monomer and approximately 50–60% w/w of vinyl acetate as a comonomer. An example of a suitable polyacrylate adhesive copolymer for use in the present invention includes, but is not limited to, that sold under the tradename of Duro Tak 87-2434 by National Starch and Chemical Co., Bridgewater, N.J., which comprises about 55% vinyl acetate comonomer.

A. Hormones

The specific hormones which may be dispersed in the adhesive polymer matrix include any hormones which are capable of controlling fertility and of being transdermally administered. With the controlled release of the hormone at a relatively steady rate over a prolonged period, typically several days and preferably one week, the subject is provided with the benefit of a steady infusion of the fertility-controlling amounts of hormones over a prolonged period. Preferably, the hormones utilized will actually be a combination of both a progestin component and an estradiol component.

It is presently preferred to use 17-beta-estradiol. It is a natural hormone and ordinarily transdermally delivered by an adaptable system of this invention at a desirable daily rate while simultaneously a presently preferred progestin, the highly active levonorgestrel, is being transdermally absorbed at a desirably daily rate. 17-beta-estradiol and levonorgestrel are compatible and can be dispersed in the matrix layer-forming polymer. The transdermal dosage unit designed for one-week therapy is required to deliver at least about 20 mcg/20 $cm^2$/day of levonorgestrel (or an equivalent effective amount of another progestin) and 20–50 mcg/20 $cm^2$/day of 17-beta-estradiol (or an equivalent effective amount of another estrogen). That amount of progestin is believed to be necessary to inhibit ovulation and that amount of estrogen is believed needed to maintain normal female physiology and characteristics.

Derivatives of 17-beta-estradiol which are biocompatible, capable of being absorbed transdermally and preferably bioconvertible to 17-beta-estradiol may also be used, if the amount of absorption meets the required daily dose of the estrogen component and if the hormone components are compatible. Such derivatives of estradiol include esters, either mono- or di-esters. The monoesters can be either 3- or 17- esters. The estradiol esters can be, illustratively speaking, estradiol-3,17-diacetate; estradiol-3-acetate; estradiol- 17-acetate; estradiol-3,17-divalerate; estradiol-3-valerate; estradiol-17-valerate; 3-mono, 17-mono and 3,17-dipivilate esters; 3-mono, 17-mono and 3,17-dipropionate esters; 3-mono, 17-mono and 3,17-di-cyclopentyl-propionate esters; corresponding cypionate, heptanoate, benzoate and the like esters; ethinyl estradiol; estrone; and other estrogenic steroids and derivatives thereof which are transdermally absorbable.

Combinations of the above or other with estradiol, for example, a combination of estradiol and estradiol-17-valerate or further a combination of estradiol, estradiol-17-valerate and estradiol-3,17-divalerate can be used with beneficial results. For example, 15–80% of each compound based on the total weight of the estrogenic steroid component can be used to obtain the desired result. Other combinations can also be used to obtain desired absorption and levels of 17-beta-estradiol in the body of the subject being treated.

The progestin hormone, as expressed above, is preferably levonorgestrel. Levonorgestrel is a potent progestin on a weight-dose basis, which is an important factor since the progestins often show a lesser degree of transdermal absorption than by 17-beta-estradiol and certain derivatives thereof. Other progestins which can be used in part or total are norgestrel, norethindrone, nore-thynodrel, hydrogesterone, ethynodiol dicetate, hydroxyprogesterone caproate, medroxyprogesterone acetate, norethindrone acetate, progesterone, megestrol, megestrol acetate, gestogen and certain others which are biocompatible, absorbable transdermally, including biocompatible derivatives of progestins which are transdermally absorbed, desirably such derivatives which are bioconvertible after transdermal absorption to the original progestin. The progestin and estrogen hormones should have high compatibility with each other.

It will be appreciated that the hormones may be employed not only in the form of the pure chemical compound, but also in admixture with other pharmaceuticals which may be transdermally applied or with other ingredients which are not incompatible with the desired objective of fertility control. Thus, simple pharmacologically acceptable derivatives of the hormones such as ethers, esters, amides, acetals, salts and the like, if appropriate, may be used. In some cases, such derivatives may actually be preferred.

The progestin compound and the estrogenic steroid are ordinarily dispersed or dissolved concurrently in fabricating the hormone-containing adhesive polymer matrix or they may be dispersed or dissolved separately.

B. Humectant/plasticizer

Preferably, a plasticizer and/or humectant is dispersed within the adhesive polymer matrix. Water-soluble polyols are generally suitable for this purpose. Preferably, polyethylene glycols, such as those having a molecular weight of from about 300 to about 1500 are used, more preferably, about 400 to about 600 molecular weight. The polyethylene glycol acts as both a plasticizer, acting to control the rigidity of the polymer matrix, as well as a humectant, acting to regulate moisture content of the formulation. Incorporation of a humectant in the formulation allows the dosage unit to absorb moisture on the surface of skin which in turn helps to reduce skin irritation and to prevent the adhesive polymer layer of the delivery system from failing.

Depending upon the hormones utilized and the drug delivery desired, a suitable amount of a plasticizer can be varied from zero to about 25 percent (by weight) based on the weight of the adhesive polymer matrix. Preferably, the amount of humectant/plasticizer utilized is less than 5%.

The polyol can be added as an aqueous solution with the polyol content varying from 10 to about 50 percent, based on the volume of the final aqueous solution.

C. Skin Permeation Enhancers

Drug molecules released from a transdermal delivery system must be capable of penetrating each layer of skin. In order to increase the rate of permeation of drug molecules, a transdermal drug delivery system must be able in particular to increase the permeability of the outermost layer of skin, the stratum corneum, which provides the most resistance to the penetration of molecules. In this regard, this invention provides a transdermal contraceptive delivery system that employs a novel combination of skin permeation enhancers. It is this novel combination of skin permeation enhancers that provides the sufficient flux of the penetrating estrogen and progestin. The skin permeation enhancers also provide the desired permeation rate ratio of these hormones to achieve the desired amount of estrogen and progestin to be released from the transdermal contraceptive delivery system and then delivered into the body to produce the desired contraceptive effect.

A combination of skin permeation enhancing agents is employed in the practice of the present invention which is a mixture of dimethyl sulfoxide (DMSO), a fatty ($C_8$–$C_{20}$) alcohol ester of lactic acid, such as lauryl lactate (Ceraphil 31), and a lower ($C_1$–$C_4$) alkanol ester of lactic acid, i.e., ethyl lactate. It is further preferred that these skin permeation enhancers be present at a weight ratio of 2.5–5:1:1, respectively. i/e/. about 4:1:1. The total amount of enhancer mixture can be up to about 50–60% w/w of the polymer matrix, preferably about 35–55% w/w. i.e., when an acrylate copolymer is used.

Fabrication of TCDS Patches

In making the hormone-containing adhesive polymer matrix, polyacrylate adhesive polymers of the formula described hereinabove are preferably utilized. The hormones are added in an amount determined by the hormone dosage and the duration of treatment desired in each dosage unit. It has been found, for example, that one part total of hormones can be satisfactorily added to about 75 parts of the polyacrylate adhesive polymer utilized in making the polymer matrix.

Preferably, prior to mixing with the polyacrylate adhesive polymer, the hormones used are dissolved and dispersed in a solution comprising a polyol, such as PEG 400 and a combination of skin permeation enhancers. More preferably, the enhancer combination and the polyol solution are combined, the hormones added thereto and subjected to mixing. The amount of enhancers utilized depends in part on the rapidity at which the hormones are to be delivered. Generally speaking, it is preferred that about 1 to about 60 percent of skin permeation enhancer based on the weight of the adhesive polymer matrix solution is suitable. More preferably, about 10 to about 50 percent of skin permeation enhancers are used. It is preferred that the hormone-containing adhesive polymer matrix contain some excess of the dispersed hormone over the dosage amount desired to be delivered thereby. Preferably, the excess is about 2 to about 10 times the desired dosage. More preferably, the excess is about 2 to about 5 times the desired dosage to be transdermally absorbed.

The adhesive polymer solution is then preferably added to the solution of hormones dispersed in the enhancer combination/polyol solution. The mixture of the polyacrylate adhesive copolymer and the polyol/enhancer/hormone solution is then thoroughly mixed using a high-torque mixer to form a homogeneous dispersion or solution of the hormones in the polyacrylate adhesive copolymer. The composition is then allowed to stand undisturbed until deaereated, i.e. for a time period of at least one hour.

Once deaerated, the adhesive polymer matrix is preferably applied to a backing layer material, such as, for example, Scotch Pak 1109, 3M Co., St. Paul Minn., and subsequently dried at 60° C. for 15 minutes. The dried adhesive polymer matrix is then laminated with a piece of release liner (such as Scotch Pak 1012, 3M Co., St. Paul, Minn.) of the same size to form a sheet of the transdermal contraceptive delivery systems. The resulting adhesive polymer matrix sheet can then be cut to form discs with desired shapes and sizes using a steel rule die and a hydraulic press. The discs generally should not exceed about 100 $cm^2$ in area. Preferably, the discs will be about 5 to 100 $cm^2$, more preferably, about 8 to about 80 $cm^2$. Most preferably, the discs will be about 10 to about 60 $cm^2$. The shape of the discs can vary; they can be circular, square, rectangular or other desired shape. The resulting transdermal contraceptive delivery system unit dosage forms are then placed in appropriate packaging for storage, such as paper and/or foil pouches, until they are to be applied in transdermal treatment.

The invention will be further described by reference to the following detailed examples.

EXAMPLE 1

Formulation and Fabrication of TCDS Patches

The physical structure (side view) of the TCDS patch formulated and fabricated in this example is illustrated in FIG. 1.

A. Formulation

The finished adhesive polymer matrix of the TCDS patch formulation utilized in this experiment has the following composition:

| Ingredients | Concentration (%) |
| --- | --- |
| 17-beta-Estradiol | 0.3 |
| Levonorgestrel | 1.1 |
| Polyethylene Glycol (PBG) 400 | 1.0 |
| Enhancer Combination | 45.0 |
| Duro Tak 87-2097 | 52.6 |

The enhancer combination contains dimethyl sulfoxide (DMSO), Ceraphil 31, and ethyl lactate at the weight ratio of 4:1:1. Ceraphil 31 is the trade name of lauryl lactate (2-hydroxy-propanoic acid, dodecyl ester) manufactured by Van Dyk, a division of Mallinckrodt, Inc. in Belleville, N.J. Duro Tak 87-2097 is the trade name of polyacrylate adhesive polymer solution manufactured by National Starch and Chemical Co., in Bridgewater, N.J. This particular grade of Duro Tak contains 2-ethylhexyl acrylate and contains approximately 55% w/w of vinyl acetate comonomer.

B. Fabrication Processes

The TCDS patches having the formulation described above are fabricated as follows. 20.2 parts (w/w) of the enhancer combination and 0.45 parts (w/w) of PEG 400 were weighed and put in a glass bottle. 17-beta-estradiol (0.135 parts w/w) and 0.49 parts (w/w) of levonorgestrel powder were added to the bottle and stirred using a magnetic stirring bar at about 200 rpm for 3 minutes in the glass bottle, or until the powder was dispersed. 78.719 parts (w/w) of Duro Tak 87-2097 (30% solid content) adhesive polymer solution was added and the bottle was sealed. The contents of the bottle was stirred using the magnetic stirring bar at about 250 rpm for 30 minutes or until a homogeneous solution was obtained. The bottle was allowed to stand for at least one hour or until all air bubbles disappeared.

A 650 µm thickness of the resulting formulation was coated on a piece of backing laminate (Scotch Pak II 09, 3M Co., St Paul, Minn.) and subsequently dried at 60° C. for 15 minutes using a laboratory coating/drying machine (Model LTSV/LTH by Werner Mathis, Switzerland). After drying, the adhesive polymer matrix became approximately 100 µm thick.

The dried adhesive polymer matrix was laminated with a piece of release liner (Scotch Pak 1012, 3M Co., St. Paul, Minn.) of the same size to form the sheet of TCDS. This sheet was cut into TCDS patches of 10 cm$^2$ using steel rule die and hydraulic press at 4000 psi. Each 10 cm2 TCDS patch was individually packaged in a paper/foil pouch and stored in the refrigerator at a temperature of 4° C.

EXAMPLE 2

In-vitro Permeation Study

To confirm that the desired skin permeation rates of both 17-beta-estradiol and levonorgestrel are achieved by the TCDS patch formulation described in Example 1, the patches manufactured were subjected to an in-vitro drug permeation study using human cadaver skin on the Valia-Chien side-by-side type skin permeation cell system (Crown Glass Co, Branchburg, N.J.). The samples taken from the receptor compartment of the diffusion cell were analyzed by high performance liquid chromatography.

Figure 2:
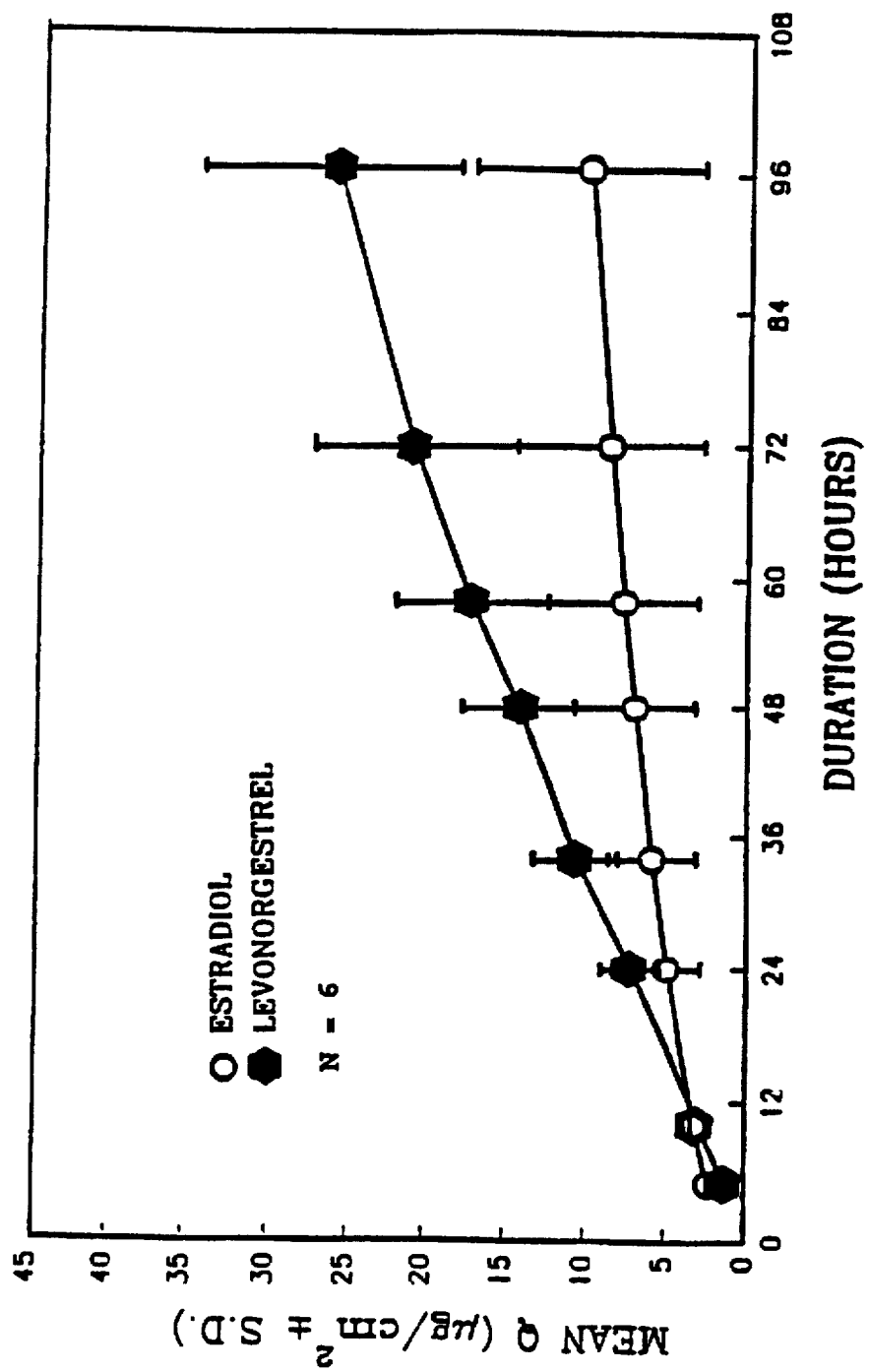
FIG. 2 is a graphical depiction of the in-vitro skin permeation profiles of both 17-beta-estradiol and levonorgestrel as delivered from the TCDS patch formulation and tested on human cadaver skin.

The in-vitro skin permeation profiles of both 17-beta-estradiol and levonorgestrel were established and are shown in FIG. 2. The skin permeation flux of each drug was subsequently calculated from the steady state of the permeation profile. Based on the results of the in-vitro study, it was determined that about 60.0±9.42 µg/day of levonorgestrel and 28.8 µg/day of 17-beta-estradiol were delivered from the 10 cm$^2$ TCDS patch fabricated in Example 1.

EXAMPLE 3

Dermal Toxicity Test

To investigate the potential of the developed TCDS patch formulation to cause skin irritation, an one-week dermal toxicity test was conducted. The test consists of an one-week primary skin irritation study on six rabbits followed by histopathological examination on each patch application. Both medicated and placebo patches of this TCDS formulation were tested on either intact or abraded skin. Based on the Draize Scale Scoring Method, the primary dermal irritation index (PDII) was given to each patch application site at 24 and 72 hours following the 7 days application period. The patches used in the primary skin irritation test were retrieved for residual drug assay to determine the amount of drugs delivered into the test animal. A summary of the daily delivery rates of levonorgestrel and estradiol is presented in Table 1, hereinbelow.

TABLE 1

Summary of daily delivery rates of levonorgestrel and estradiol

| | | Daily Delivery Rate (µg/day ± S.D.) Rabbit Skin | |
| --- | --- | --- | --- |
| | Target | Intact (N = 6) | Abraded (N = 6) |
| Levonorgestrel | 50 | 64.0 ± 32.88 | 61.8 ± 39.22 |
| Estradiol | 25 | 37.0 ± 19.77 | 35.1 ± 26.70 |

The results of the primary skin irritation test on placebo and medicated TCDS patch formulation are summarized in Tables 2 and 3. The PDII scores for placebo and medicated TCDS patch formulation were 1.0 and 1.85, respectively. Since the PDII scores are on a scale of 1.0 to 8.0, this TCDS patch formulation has very minimal potential to cause skin irritation.

TABLE 2

Draize Scores of Primary skin irritation test on placebo formulation of TCDS patches

| | 1/15/93 24 hours | | | | 1/17/93 72 hours | | | |
| --- | --- | --- | --- | --- | --- | --- | --- | --- |
| | Intact skin | | Abraded skin | | Intact skin | | Abraded skin | |
| Animal # | Erythema | Edema | Erythema | Edema | Erythema | Edema | Erythema | Edema |
| 27492 | 1 | 0 | 1 | 0 | 1 | 0 | 1 | 0 |
| 27493 | 1 | 0 | 1 | 0 | 1 | 0 | 1 | 0 |
| 27494 | 1 | 0 | 1 | 0 | 1 | 0 | 1 | 0 |
| 27495 | 1 | 0 | 1 | 0 | 1 | 0 | 1 | 0 |
| 27496 | 1 | 0 | 1 | 0 | 1 | 0 | 1 | 0 |
| 27497 | 1 | 0 | 1 | 0 | 1 | 0 | 1 | 0 |
| Mean | 1.0 | 0.0 | 1.0 | 0.0 | 1.0 | 0.0 | 1.0 | 0.0 |

Note:
Primary dermal irritation index (PDII) = 1.00

TABLE 3

Draize Scores of Primary skin irritation test on medicated formulation of TCDS patches

| | 1/15/93 24 hours | | | | 1/17/93 72 hours | | | |
| --- | --- | --- | --- | --- | --- | --- | --- | --- |
| | Intact skin | | Abraded skin | | Intact skin | | Abraded skin | |
| Animal # | Erythema | Edema | Erythema | Edema | Erythema | Edema | Erythema | Edema |
| 27492 | 1 | 0 | 1 | 0 | 1 | 0 | 1 | 0 |
| 27493 | 2 | 1 | 1 | 1 | 2 | 0 | 1 | 0 |
| 27494 | 2 | 2 | 2 | 2 | 2 | 0 | 2 | 0 |
| 27495 | 2 | 2 | 2 | 2 | 1 | 0 | 2 | 0 |
| 27496 | 1 | 1 | 1 | 1 | 1 | 0 | 1 | 0 |
| 27497 | 1 | 0 | 1 | 0 | 1 | 0 | 1 | 0 |
| Mean | 1.5 | 1.0 | 1.3 | 1.0 | 1.3 | 0.0 | 1.3 | 0.0 |

Note:
Primary dermal irritation index (PDII) = 1.00

The results of histopathological examination also revealed that both placebo and medicated patch formulations of TCDS caused only mild to moderate degree of inflammation to the test animal (Table 4, below). In addition to low skin irritation potential, the test animals were found to have no significant change in body weight and no signs of intoxication were observed.

TABLE 4

Scores of histopathological examination on the placebo and medicated TCDS patches in the dermal toxicity test.

| | Intact Skin | | Abraded-Skin | |
| --- | --- | --- | --- | --- |
| Animal # | Control | Test | Control | Test |
| 27492 | 1+ | 2+ | 1+ | 2+ |
| 27493 | 2+ | 2+ | 2+ | 1+ |
| 27494 | 3+ | 2+ | 2+ | 3+ |
| 27495 | 1+ | 2+ | 1+ | 3+ |
| 27496 | 1+ | 3+ | 2+ | 2+ |
| 27497 | 1+ | 2+ | 2+ | 3+ |
| Mean | 1.5 | 2.2 | 1.7 | 2.3 |

1+ = Minimal to mild
2+ = Mild to moderate
3+ = Moderate
4+ = Severe

Daily delivery rates of levonorgestrel into the rabbits used in the dermal toxicity study were 64.0±32.88 µg/day and 61.8±39.22 µg/day, respectively, for intact and abraded skin. The in vivo delivery rate of levonorgestrel in the rabbit seems to correlate very well with the in vitro delivery rate (Table 1). For 17-beta-estradiol, the daily delivery rate is 3 7.0±19.77 µg/day and 3 5.1±26.70 µg/day, respectively, for intact and abraded skin. This in vivo delivery rate of 17-beta-estradiol is higher than skin permeation rate obtained in the in vitro study.

EXAMPLE 4

Phase I Clinical Study

A phase I bioavailability-dose proportionality clinical study on the TCDS patch formulation was conducted using fertile Chinese women. In this study, healthy female subjects of child-bearing age were randomly divided into 4 groups in a 4-way parallel study design (See Table 5). The study consists of three menstrual cycles which are sequentially arranged as pre-treatment, treatment and post-treatment cycles. During the pre-treatment cycle, the 48 recruited subjects were given placebo TCDS patches to study the wearability (including skin irritation and adhesion tests) while they were being screened against the inclusion/ exclusion criteria specified in the clinical protocol. During the treatment cycle, each of the 8 subjects in Group A, B and C received weekly application of 1, 2 or 3 pieces of 10 cm² TCDS patches, respectively, while each subject in Group D received one oral contraceptive pill (each pill contains 150 µg of levonorgestrel and 35 µg of ethynyl estradiol) per day as reference.

TABLE 5

Study Design of the phase I clinical study on TCDS patch formulation in fertile Chinese women

| CYCLE | CLINICAL ACTIVITIES | ASSAY & MEASUREMENTS |
|---|---|---|
| 1. Pre-Treatment (21 + 7 days) | a. recruit 48 women | Basal body temperature |
| | b. admit 32 subjects | E2, P, LH and FSH |
| | c. randomly divide the subjects | Hematological determinations |
| | d. initiate wearability test on Groups A, B and C with placebo patches | Clinical chemistry Urinalysis |
| | e. hormonal base line establishment on Groups A, B and C | Skin Irritation test Adhesion Test |
| 2. Treatment (21 + 7 days) | a. conduct a 4-way parallel bioavailability-dose proportionality study: | LNG, E2, P, LH, and FSH Hematological determinations Clinical chemistry Urinalysis |
| | Group A: 1 × 10 cm² patch/week | |
| | Group B: 2 × 10 cm² patch/week | Recording adverse reactions |
| | Group C: 3 × 10 cm² patch/week | |
| | Group D: 1 tablet/day | |
| 3. Post-treatment (21 days) | a. recovery of normal menstrual cycle | LNG, E2, P, LH, and FSH |
| | b. drug recovery study on the used patches to determine the amount of drug delivered | Hematological determinations Clinical chemistry Urinalysis Recording adverse reactions |

Blood samples obtained from these three cycles of studies were assayed by radioimmunoassay (RIA) methods for their serum concentration of levonorgestrel, estradiol, progesterone, luteinizing hormone (LH) and follicle stimulating hormone (FSH). Ultrasonic measurement of follicle size and endometrium thickness measurement were also performed during the mid-treatment cycle. Bioavailability of levonorgestrel was assessed by the serum levonorgestrel profile of each subject group. Suppression of post-ovulatory progesterone peak and mid-cycle surges of LH and FSH provided hormonal indications of ovulation inhibition. Contraceptive efficacy of the TCDS patch formulation in this clinical study was assessed according to the results of hormonal indications of ovulation inhibition, follicle size and endometrium changes.

The placebo TCDS patches were found very well tolerated by the women subjects in all three study groups as indicated by the low (less than 1.0 on the scale of 8.0) PDII values obtained during the pre-treatment cycle (Table 6, below).

TABLE 6

Primary dermal irritation index of the placebo TCDS patches obtained in the pre-treatment cycle phase I clinical study

| Subject Group | Erythema | Edema | PDII |
|---|---|---|---|
| Group A (n = 8) | 0.10 | 0 | 0.10 |
| Group B (n = 7) | 0.10 | 0 | 0.10 |
| Group C (n = 7) | 0.42 | 0.12 | 0.53 |

It was also found that the placebo TCDS patches stayed very well (99.5% of mean survival rate) on the skin of all three groups of the women subjects in the real-life wearing situation during the pretreatment cycle of the phase I clinical study (Table 7, below).

TABLE 7

Mean patch survival rate of the placebo TCDS patch formulation during the pre-treatment cycle of the phase I clinical study

| Subject Group | Position | Total # of days/ Maximum # of days | Patch Survival rate |
|---|---|---|---|
| Group A | Right Abdomen | 96/98 | 98.8% |
| | Left Abdomen | 69/70 | 98.6% |
| Group B | Right Abdomen | 168/168 | 100% |
| | Left Abdomen | 126/126 | 100% |
| Group C | Right Abdomen | 230/231 | 99.6% |
| | Left Abdomen | 210/210 | 100% |

Mean Survival Rate = 99.5%

Figure 3:
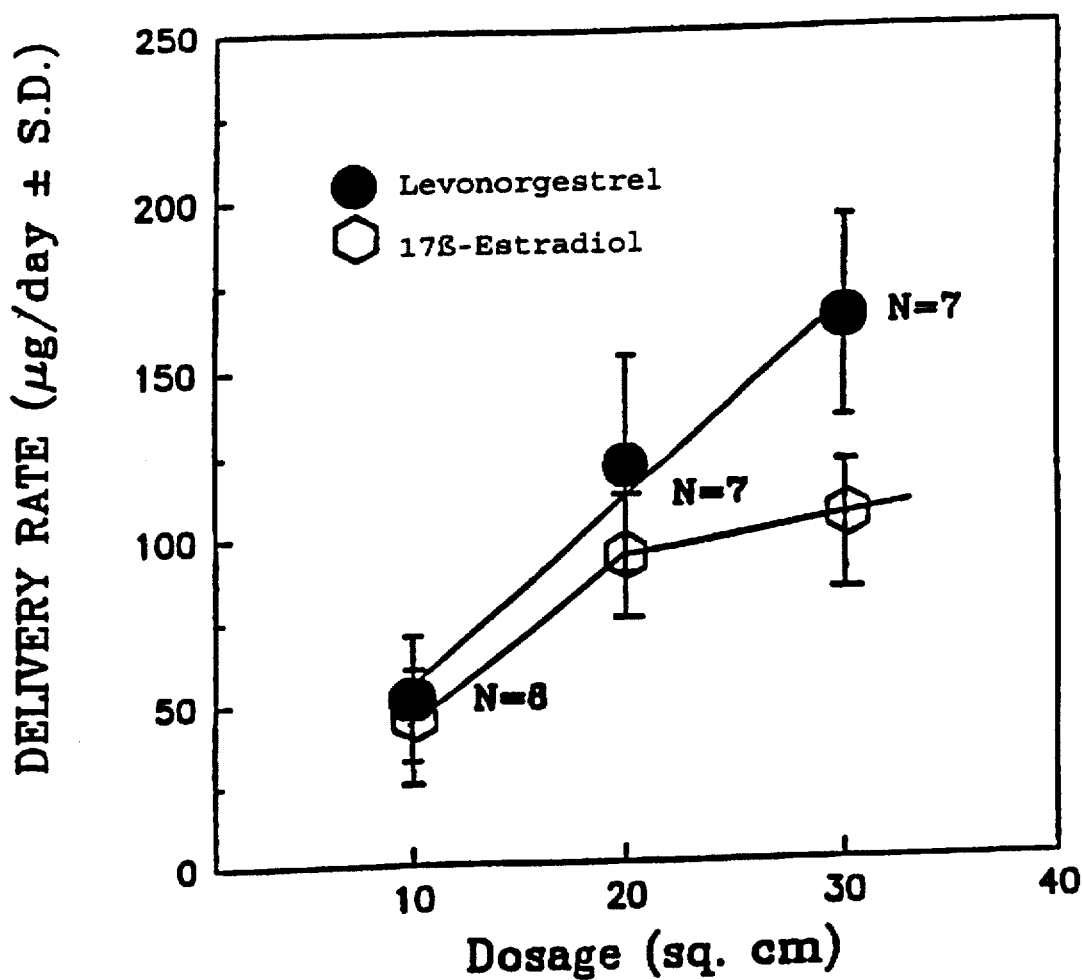
FIG. 3 is a graphical depiction of the relationship between the daily delivery of levonorgestrel and the dosage of levonorgestrel in the TCDS patches used in the phase I clinical study.

Residual drug assays from the used patches retrieved from the phase I clinical study allowed the daily delivery rate of both levonorgestrel and estradiol to be calculated. FIG. 3 and Table 8, below, show that the daily delivery rate of levonorgestrel is linearly proportional to the increase in dosage of TCDS patches. However, this linear relationship between the daily delivery rate of estradiol and dosage was established only for the dosages of the first and second pieces of 10 cm² TCDS patches and does not extent to the third pieces of TCDS patch tested.

TABLE 8

Summary of daily delivery rates levonorgestrel and estradiol.

| | | Daily Delivery Rate (µg/day ± S.D.) | | |
|---|---|---|---|---|
| | Target | Group A | Group B | Group C |
| Levonorgestrel | 50 | 51.0 ± 19.12 | 121.1 ± 32.34 | 163.7 ± 29.48 |
| Estradiol | 25 | 42.1 ± 16.32 | 89.7 ± 28.4 | 110.4 ± 28.61 |

Figure 4:
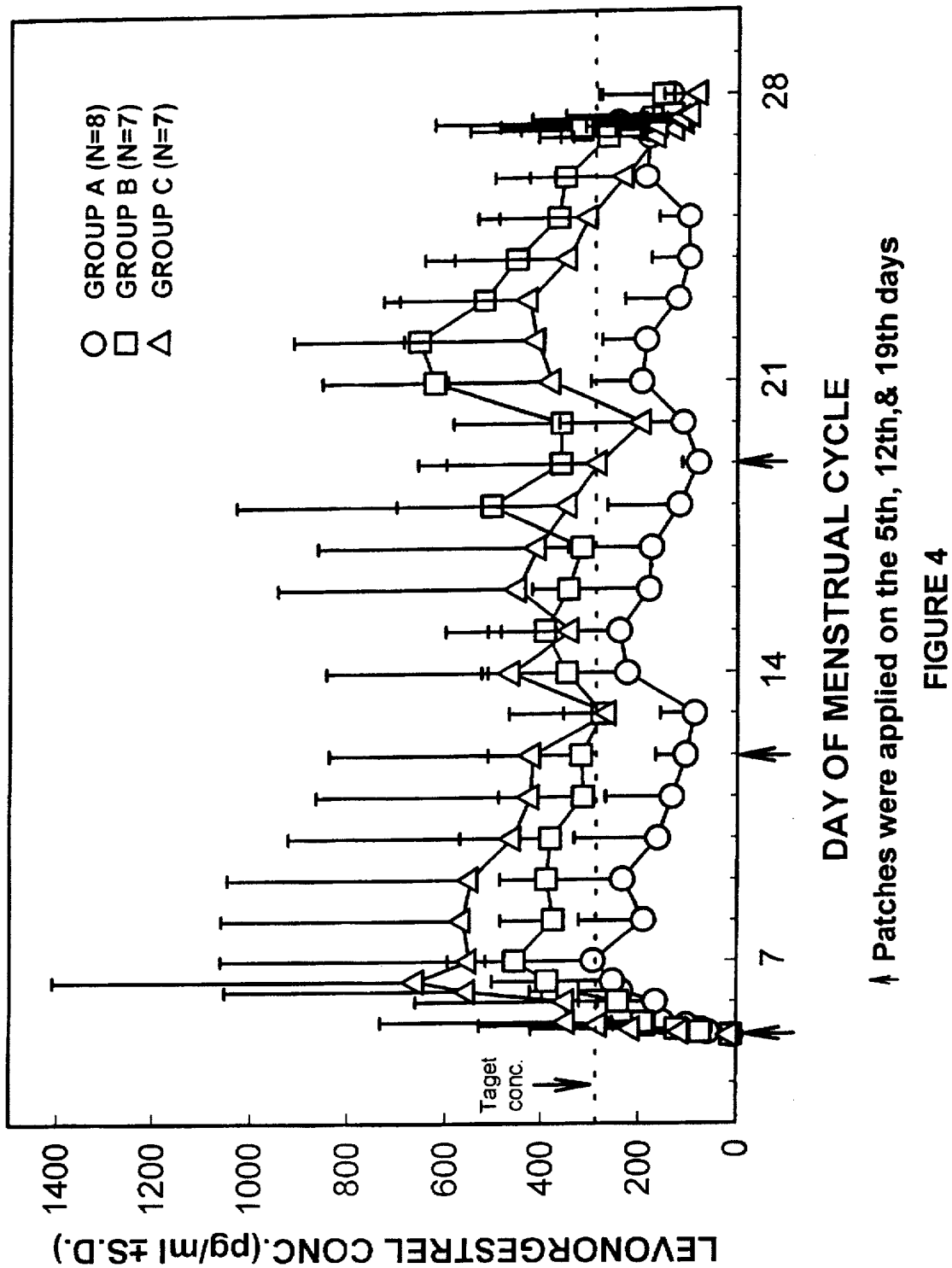
FIG. 4 is a graphical depiction of the serum profiles of levonorgestrel that resulted from the weekly application of 1, 2 or 3 TCDS patches (each 10 $cm^2$) to the subjects of Group A, B or C, respectively.

Serum profiles of levonorgestrel resulted from the weekly application of 1, 2 or 3 TCDS patches (each 10 cm²) to the subjects of Group A, B or C, respectively, are shown in FIG. 4. The TCDS patches formulation produced a levonorgestrel serum concentration above the target concentration throughout the three weeks of patch application on the subjects in Group B and Group C. The serum levonorgestrel profiles obtained suggest that a high percentage of subjects in Groups B and C achieved ovulation.

Figure 5A:
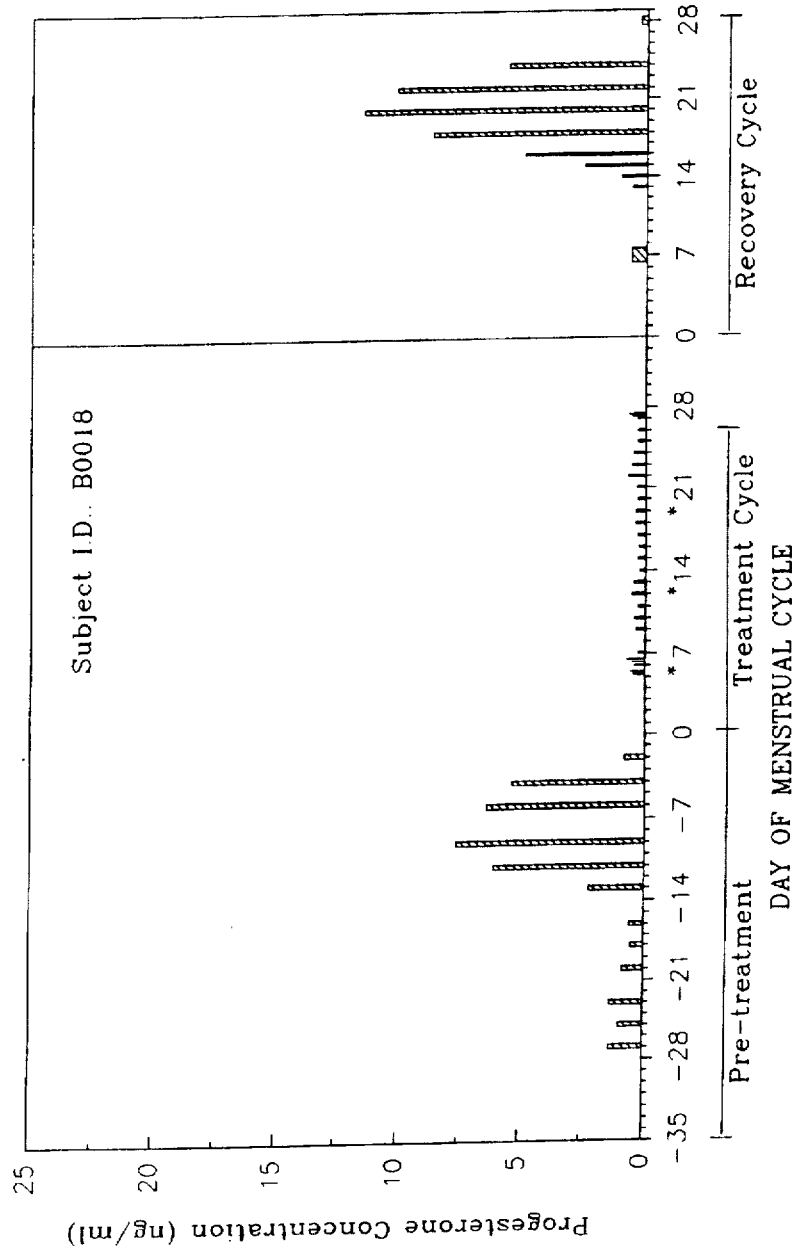
FIG. 5 is a graphical depiction of the serum profiles of progesterone, FSH and LH for subject ID#B0018.
Figure 5B:
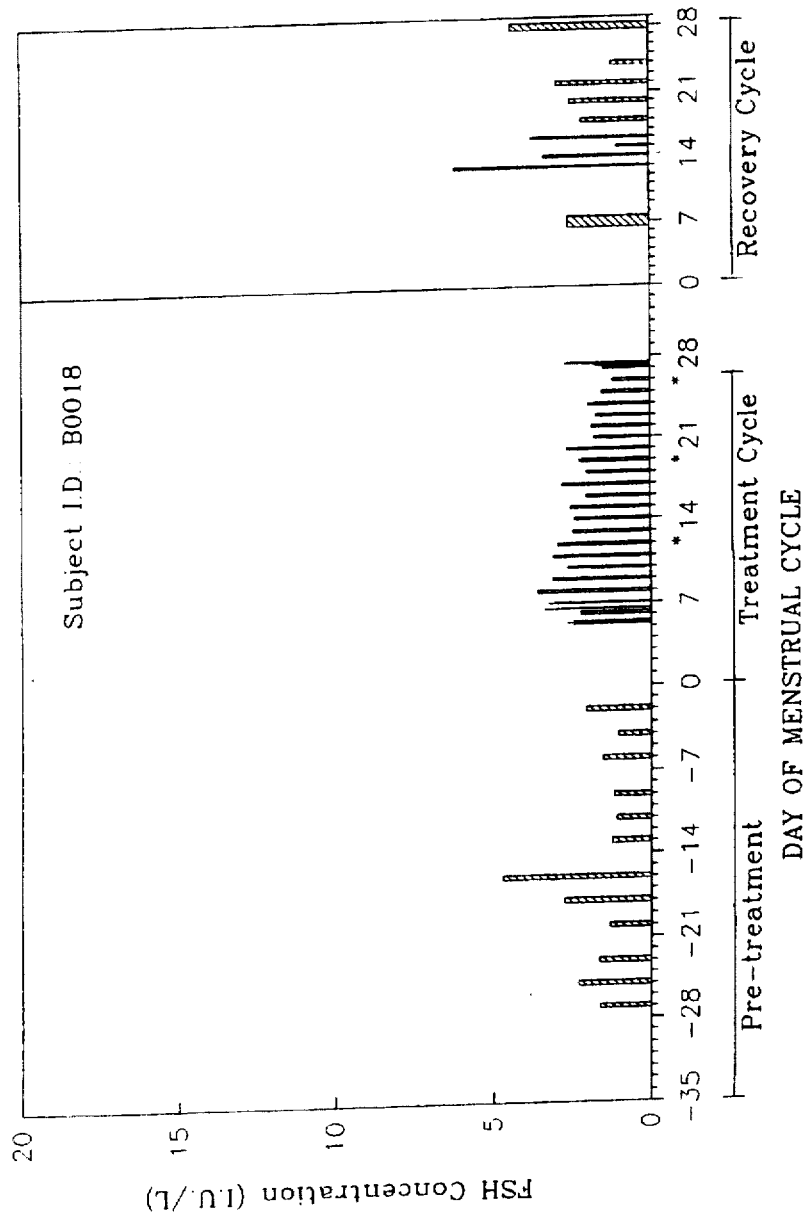
Figure 5C:
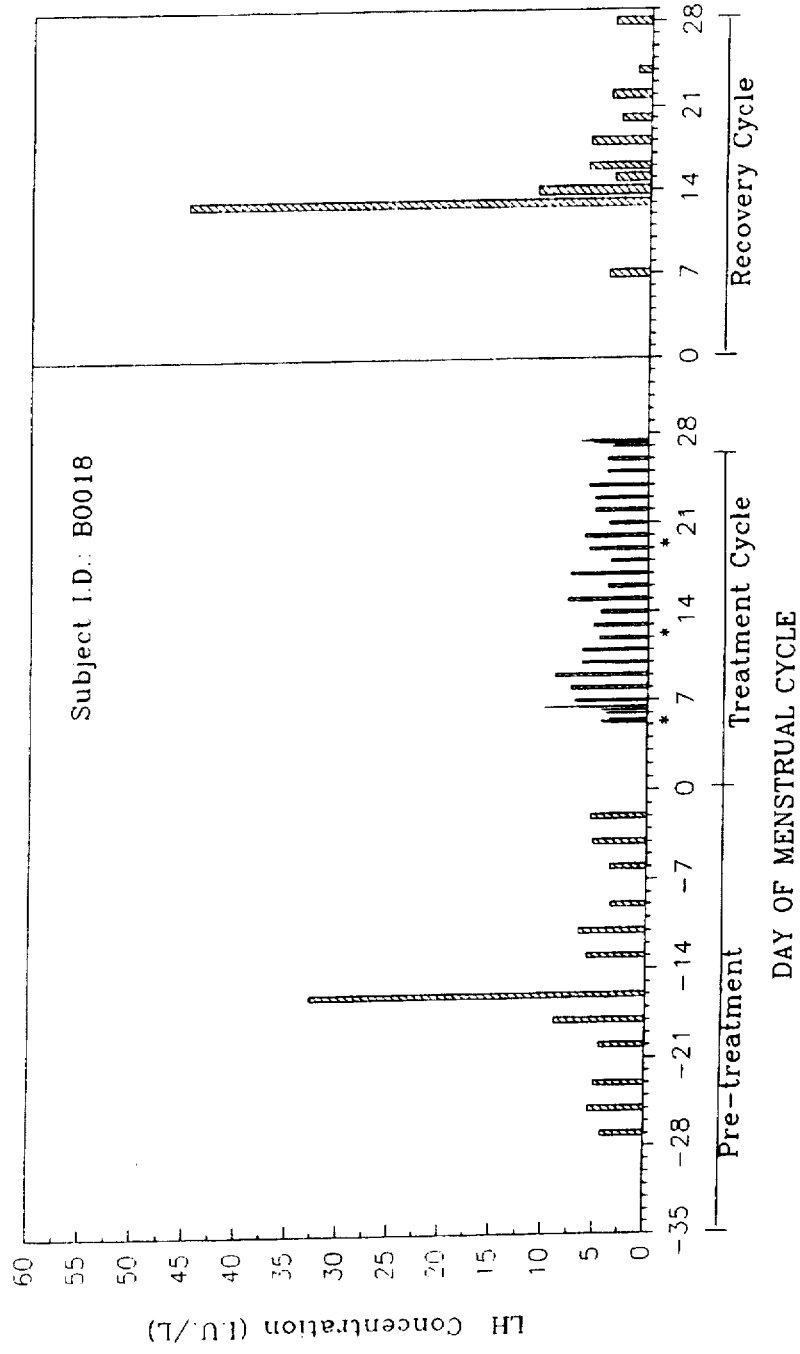

Serum profiles of progesterone, FSH and LH for each of the subjects that participated in this clinical study were examined for their indication of ovulation inhibition. FIG. 5, for example, shows that subject (ID#B0018) had a normal menstrual cycle during the pretreatment cycle as indicated by the mid-cycle surges of serum FSH and LH and the post-ovulatory elevation of serum progesterone. After the TCDS patches (2×10 cm² for 3 weeks) were applied, all three serum hormonal peaks were completely suppressed during the treatment cycle. Moreover, the subject's menstrual cycle was found to return to normal after the termination of TCDS patch application as indicated by the reappearance of the mid-cycle surges of serum FSH and LH and the post-ovulatory rise of the serum progesterone.

Table 9 summarizes the results of the examination of serum progesterone, FSH and LH profiles of each subject of groups A, B and C in this 3-cycle long phase I clinical study. It was found that 7 out of 7 subjects in Group A, 6 out of 7 subjects in Group B and 7 out of 7 subjects in Group C showed the occurrence of ovulation inhibition as indicated by the hormonal indicators. Subject ID#A0025 showed the occurrence of ovulation as indicated by the mid-cycle FSH and LH surges, however, the lack of progesterone surge suggested an abnormal hormonal condition in the ovary. Subject ID#B0014 showed delayed maturation of the ovum which may have resulted in follicular rupture. Observation of the endometrium changes of these subjects provided supplemental evidence that these two subjects were infertile. As the results of these indications and evidence, contraceptive efficacy of 100% has been achieved by all three groups of the subjects that received a TCDS patch regimen.

TABLE 9

Summary of hormonal indications of ovulation inhibition for the participants in the phase I clinical study

| Subject ID # | Hormonal Indications of Ovulation Inhibition | | |
|---|---|---|---|
| | P | LH | FSH |
| A0001 | + | + | + |
| A0005 | − | + | + |
| A0009 | + | + | + |
| A0013 | + | + | + |
| A0017 | + | + | + |
| A0025* | + | − | − |
| A0029 | + | + | + |
| A0033 | + | + | + |
| Group A: 7/8 subjects show ovulation inhibition. Efficacy: 8 out of 8 = 100% | | | |
| B0002 | + | + | + |
| B0006 | + | + | + |
| B0010 | + | + | + |
| B0014* | − | + | + |
| B0018 | + | + | + |
| B0022 | + | + | + |
| B0026 | + | + | + |
| Group B: 6/7 subjects show ovulation inhibition. Efficacy: 7 out of 7 = 100% | | | |
| C0003 | + | + | + |
| C0007 | + | + | + |
| C0011 | + | + | + |

TABLE 9-continued

Summary of hormonal indications of ovulation inhibition for the participants in the phase I clinical study

| Subject ID # | Hormonal Indications of Ovulation Inhibition | | |
|---|---|---|---|
| | P | LH | FSH |
| C0019 | + | + | + |
| C0023 | + | + | + |
| C0027 | + | + | + |
| C0031 | + | + | + |
| Group C: 7/7 subjects show ovulation inhibition. Efficacy: 7 out of 7 = 100% | | | |

+ Indicates ovulation inhibition
− Indicates no ovulation inhibition
Efficacy is assessed based on ovulation inhibition, follicle size and endometrium thickness.

EXAMPLE 5

Phase II Clinical Study

Due to the success of the phase I clinical-study of the TCDS patch formulation described in Example 1, a phase II clinical study was launched. In this study, each subject received one 2×10 cm² TCDS patch per week for three consecutive weeks per cycle. As of April 1995, more than 150 Chinese women of child-bearing age had participated in the study for a total of 2,000 cumulative months of study. The subjects remained healthy, fertile and sexually active during this study. Contraceptive efficacy of 96% has been achieved in this phase II clinical study for a time period of greater than one year.

All patents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A transdermal contraceptive delivery system comprising:
 a) a backing layer which is substantially impermeable to the fertility-controlling estrogen and progestin hormones to be delivered transdermally; and
 b) an adhesive polymer matrix affixed to said backing layer comprising on a weight percentage basis from about 0.1% to about 25% humectant/plasticizer, from about 30 to about 60 percent of a combination of skin permeation enhancing agents which is a mixture consisting of dimethyl sulfoxide, a fatty ($C_8$–$C_{20}$) alcohol ester of lactic acid and a lower ($C_1$–$C_4$) alkyl ester of lactic acid present in an about 2.5–5:1:1 ratio, respectively, and an effective amount of fertility-controlling estrogen and progestin hormones, wherein said hormones provide at least minimum effective daily doses of said hormones to effect fertility control.

2. The transdermal contraceptive delivery system of claim 1 wherein the polymer matrix comprises a polyacrylate adhesive copolymer.

3. The transdermal contraceptive delivery system of claim 2 wherein the polyacrylate adhesive copolymer comprises a 2-ethylhexyl acrylate monomer.

4. The transdermal contraceptive delivery system of claim 3 wherein the polyacrylate adhesive copolymer further comprises about 3 to 60% w/w vinyl acetate.

5. The transdermal contraceptive delivery system of claim 4 wherein the adhesive polymer matrix has a cross-sectional dimension of from about 10 to 300 microns.

6. The transdermal contraceptive delivery system of claim 1 wherein said fatty alcohol ester of lactic acid is lauryl lactate.

7. The transdermal contraceptive delivery system of claim 6 wherein said lower alkyl ester of lactic acid is ethyl lactate.

8. The transdermal contraceptive delivery system of claim 7 wherein said dimethyl sulfoxide, lauryl lactate and ethyl lactate are present in a ratio of about 4:1:1, respectively.

9. The transdermal contraceptive delivery system of claim 1 wherein said estrogen hormone is selected from the group consisting of 17-beta-estradiol and ethynyl estradiol and said progestin hormone is levonorgestrel.

10. The transdermal contraceptive delivery system of claim 9 wherein said estrogen hormone is 17-beta-estradiol and said progestin hormone is levonorgestrel.

11. The transdermal contraceptive delivery system of claim 10 wherein the 17-beta-estradiol is transdermally delivered at a rate of at least 20 µg but no more than 50 µg per day for at least a term of more than one day to about one week, and the levonorgestrel is transdermally delivered at a rate of about 20 µg per day for at least a term of more than one day to about one week.

12. The transdermal contraceptive delivery system of claim 1 wherein said humectant/plasticizer is a polyethylene glycol.

13. The transdermal contraceptive delivery system of claim 12 wherein said polyethylene glycol is present in an amount of from about 0.25 to about 2.5% of the adhesive polymer matrix.

14. A method of controlling fertility by applying to the skin of a subject desiring such treatment a transdermal contraceptive delivery system comprising:

a) a backing layer which is substantially impermeable to the fertility-controlling estrogen and progestin hormones to be delivered transdermally; and b) an adhesive polymer matrix affixed to said backing layer comprising on a weight percentage basis from about 0.1% to about 25% humectant/plasticizer, from about 30 to about 60 percent of a combination of skin permeation enhancing agents which is a mixture consisting of dimethyl sulfoxide, a fatty ($C_8$-$C_{20}$) alcohol ester of lactic acid and a lower ($C_1$-$C_4$) alkyl ester of lactic acid present in an about 2.5–5:1:1 ratio, respectively, and an effective amount of fertility-controlling estrogen and progestin hormones, wherein said hormones provide at least minimum effective daily doses of said hormones to effect fertility control, to provide at least the minimum effective dose amounts of levonorgestrel and 17-beta-estradiol for about the first three weeks of a menstrual cycle for successive menstrual cycles for a period extending as fertility control is desired.

15. The method of claim 14 wherein the adhesive polymer matrix comprises a polyacrylate adhesive copolymer.

16. The method of claim 15 wherein the polyacrylate adhesive copolymer comprises a 2-ethylhexyl acrylate monomer.

17. The method of claim 16 wherein the polyacrylate adhesive copolymer further comprises about 3 to 60% w/w vinyl acetate.

18. The method of claim 17 wherein the adhesive polymer matrix has a cross-sectional dimension of from about 10 to 300 microns.

19. The method of claim 14 wherein said fatty alcohol ester of lactic acid is lauryl lactate.

20. The method of claim 19 wherein said lower alkyl ester of lactic acid is ethyl lactate.

21. The method of claim 20 wherein said dimethyl sulfoxide, lauryl lactate and ethyl lactate are present in a ratio of about 4:1:1, respectively.

22. The method of claim 14 wherein said estrogen hormone is selected from the group consisting of 17-beta-estradiol and ethynyl estradiol and said progestin hormone is levonorgestrel.

23. The method of claim 22 wherein said estrogen hormone is 17-beta-estradiol and said progestin hormone is levonorgestrel.

24. The method of claim 22 wherein the 17-beta-estradiol is transdermally delivered at a rate of at least 20 µg but no more than 50 µg per day for at least a term of more than one day to about one week, and the levonorgestrel is transdermally delivered at a rate of about 20 µg per day for at least a term of more than one day to about one week.

25. The method of claim 14 wherein said humectant/plasticizer is a polyethylene glycol.

26. The method of claim 25 wherein said polyethylene glycol is present in an amount of from about 0.25 to about 2.5% of the adhesive polymer matrix.

* * * * *